United States Patent [19]
Simon et al.

[11] Patent Number: 5,089,526
[45] Date of Patent: Feb. 18, 1992

[54] ANTIARRHYTHMIC CLASS III PROCESS

[75] Inventors: Arthur Simon, Pomona, N.Y.; Jeff A. Thomis, Liederkerke, Belgium

[73] Assignee: Bristol-Myers Company, New York, N.Y.

[21] Appl. No.: 945,915

[22] Filed: Dec. 23, 1986

Related U.S. Application Data

[63] Continuation-in-part of Ser. No. 716,528, Mar. 17, 1985, abandoned, which is a continuation of Ser. No. 497,368, May 23, 1983, abandoned.

[51] Int. Cl.$^5$ .............................................. A61K 31/18
[52] U.S. Cl. ...................................... 514/605; 514/821
[58] Field of Search ................................. 514/605, 821

[56] References Cited

U.S. PATENT DOCUMENTS 3,341,584  9/1967  Larsen et al. ........................ 260/556

OTHER PUBLICATIONS

N. Edvardsson, *Current Therapeutic Research*, 28, No. 1 Supplement, pp. 113S–118S, Jul. 1980.
Keefe et al, *Drugs*, 22, 363–400 (1981).
N. Edvardsson et al., *European Heart Journal*, 1, 335–343 (1980).
D. E. Ward et al., *Clin. Cardiol.*, 2, 185–191 (1979).
D. P. Myburgh et al., *SA Medical Journal*, 295–298 (Aug. 1979).
L. D. Davis et al., *Research in Physiology*, 99–114, A. Gaggi Publisher, Bologna (1971).
B. N. Singh et al., *Br. J. Pharmac.*, 39, 675–687 (1970).
D. C. Kvam et al., *J. Pharm. Exper. Therap.*, 149(2), 183–193 (1965).
J. V. Levy et al., *Proc. Soc. Exp. Biol. Med.*, 122, 373–379 (1966).
P. Somani et al., *J. Pharm. Exper. Therap.*, 164(2), 317–326 (1968).
D. A. Lathrop, *Can. J. Physiol. Pharmacol.*, vol. 63, 1506–1512 (1985).

*Primary Examiner*—Frederick E. Waddell
*Assistant Examiner*—Kevin E. Weddington
*Attorney, Agent, or Firm*—Kenyon & Kenyon

[57] ABSTRACT

A process is provided for preventing or ameliorating arrhythmia by administering to mammals, including man, an effective dose of d-sotalol to lengthen the action potential duration of cardiac cell without blockade of beta-adrenergic receptor sites.

5 Claims, No Drawings

ANTIARRHYTHMIC CLASS III PROCESS

CROSS-REFERENCE TO RELATED APPLICATIONS

This is a continuation-in-part of Ser. No. 716,528 filed Mar. 17, 1985, now abandoned, which is a continuation of Ser. No. 497,368 filed May 23, 1983, now abandoned.

BACKGROUND OF THE INVENTION

This invention relates to a process for treating arrhythmias, and more particularly, to process for preventing or ameliorating arrhythmia by lengthening cardiac cell action potential duration and refractory period without beta-adrenergic blockade by administering an effective dose of dextrorotatory 4-(2-isopropylamino-1-hydroxyethyl)-methanesulfonanalide or a pharmaceutically acceptable acid addition salt thereof.

The racemic form of 4-(2-isopropylamino-1hydroxyethyl)-methanesulfonanilide, disclosed and claimed in Larsen, et al., U.S. Pat. No. 3,341,584, is a recognized beta-blocking agent known in the biological literature as sotalol or MJ 1999. Pharmacologically, beta-blocking compounds reduce sympathetic excitation of the heart and in this respect are considered antiarrhythmics.

Antiarrhythmic drugs are commonly divided into four classes according to their electrophysiological mode of action. Refer to N. Edvardsson, *Current Therapeutic Research*, 28, No. 1 Supplement, pages 113S-118S, July, 1980, and Keefe, et al., *Drugs*, 22, 363-400 (1981) for background information of classification first proposed by E. M. Vaughn Williams: classification of antiarrhythmic drugs, in "Symposium of Cardiac Arrhythmias," pages 449-472, Sandoe, et al., (Eds.) A. B. Astra, Soederlalje, Sweden (1970).

Classification of Antiarrhythmic Drugs

I. Local Anesthetic Effect
II. Beta-receptor Blockade
III. Prolongation of Action-potential Duration
IV. Calcium Antagonism Class I agents usually have little or no effect on action potential duration and exert local anesthetic activity directly at cardiac cell membrane. Class II agents show little or no effect on the action potential and exert their effects through competitive inhibition of beta-adrenergic receptor sites thereby reducing sympathetic excitation of the heart. Class III agents are characterized by their ability to lengthen the action potential duration thereby preventing or ameliorating arrhythmias. Class IV agents are those which have an antiarrhythmic effect due to their actions as calcium antagonists.

According to the above classification, sotalol is a class III antiarrhythmic agent. N. Edvardsson, supra.; N. Edvardsson, et al., *European Heart Journal*, 1, 335-343 (1980); D. E. Ward, et al., *Clin. Cardio.*, 2, 185-191 (1979); D. P. Myburgh, et al., *SA Medical Journal*, 295-298 (Aug., 1979); L. D. Davis, et al., *Research in Physiology*, 99-114, A. Gaggi Publisher, Bologna (1971); B. N. Singh, et al., *Br. J. Pharma.*, 39, 675-687 (1970). Sotalol is also a Class II antiarrhythmic agent in that it reduces sympathetic excitation of the heart by beta-blockade.

The active ingredient of the instant process "dextrorotatory 4-(2-isopropylamino-1-hydroxyethyl)methanesulfonanilide" and the corresponding levorotatory stereoisomer have been the subject of biological study and representative publications are listed below. As used in the literature and herein, the racemate form of 4-(2-isopropylamino-1-hydroxyethyl)methanesulfonanilide is at times referred to as sotalol or dl-sotalol, the dextrorotatory isomer as d-sotalol or (+)-sotalol, and the levorotatory isomer as l-sotalol or (-)-sotalol.

D. C. Kvam, et al., *J. Pharm. Exper. Therap.*, 149(2), 183-192 (1965) reported that l-sotalol was about 20-30 times more potent than d-sotalol in preventing certain metabolic effects such as epinephrine-induced hyperglycemia or hyperlipidemia.

J. V. Levy, et al., *Proc. Soc. Exp. Biol. Med.*, 122, 373-379 (1966) studied the inotropic and chronotropic effects of sotalol, d-sotalol, and l-sotalol on rabbit heart atrial preparations and determined that, compared to the racemate, d-sotalol was substantially weaker as a beta-blocking agent whereas l-sotalol was considerably more potent.

P. Somani, et al., *J. Pharm. Exper. Therap.*, 164(2), 317-325 (1968) investigated the antiarrhythmic activity of dextro- and levo- rotatory isomers of sotalol in the dog and found that l-sotalol, considered the active isomer in terms of blockade of beta-receptors, is also the active isomer for specific antiarrhythmic activity (i.e. blockade of adrenergically-induced arrhythmia—Class II). Cardiac arrhythmias induced by oubain or coronary artery litigation were not suppressed by either isomer demonstrating a lack of non-specific antiarrhythmic activity (Class I) seen with other beta-adrenergic blocking agents such as the levorotatory and dextrorotatory isomers of pronetholol, propanolol and H56/28. The authors concluded that the antiarrhythmic effects of sotalol are a reflection of the specific beta-receptor blocking action of the drug.

Thus, with respect to antiarrhythmic use, there is little in the prior art which would suggest that d-sotalol effectively lengthens cardiac cell action potential duration given the relative inactivity of d-sotalol as a beta-blocking agent.

DESCRIPTION OF THE INVENTION

The present invention is based upon the discovery that d-sotalol lengthens the action potential duration of cardiac cells and is thereby useful in treating heart arrhythmias. In accordance with the invention, a process is provided for preventing or ameliorating arrhythmia in a mammal comprising administering an effective dose of d-sotalol or a pharmaceutically acceptable acid addition salt thereof essentially free of l-sotalol (i.e. less than 1% and preferably less than 0.5%) to a mammal in need thereof to lengthen the action potential duration of ventricular muscle cell without significant beta-adrenergic blockade. More particularly, there is provided an antiarrhythmic process comprising administering an effective dose of d-sotalol essentially free of l-sotalol or a pharmaceutically acceptable acid addition salt thereof to a mammal having arrhythmia or susceptible to arrhythmia to lengthen the action potential duration of cardiac cell sufficiently to produce an antiarrhythmic effect without blocking beta-adrenergic receptor sites.

Administration of d-sotalol can be carried out orally or parenterally (e.g., intravenous injection) employing liquid or solid form pharmaceutical preparations containing d-sotalol as free base or in the form of a pharmaceutically acceptable acid addition salt in combination with a pharmaceutically acceptable carrier.

The dosage administered depends upon the age, state of health, the weight of the recipient, the extent of the disease, the nature of further treatments possible carried out simultaneously and frequency of the treatment. Usually, the effective dose of d-sotalol ranges from 0.3–8.6 mg/kg body weight of said mammal. In the case of a human, a dose of from 20 to 600 mg per patient is given from 1 to 4 times per day with oral administration preferred. When d-sotalol is administered by the preferred oral route, a larger quantity of d-sotalol is required, preferably 160–480 mg once or twice/day, to produce the same effect as a smaller quantity given parenterally, for example by intravenous injection.

Clinical evaluation of d-sotalol in antiarrhythmic patients has established that the most preferred effective intravenous dose ranges from 0.75–2.0 mg/kg body weight with oral unit doses ranging from 100–200 mg.

The instant process is carried out in accordance with good clinical practice, that is, d-sotalol is administered at an effective dose that will produce an increase in action potential duration without causing any harmful or untoward side effects.

Conventional techniques for studying arrhythmias including ambulatory electrocardiography with computer-assisted analysis and programmed stimulation techniques for arrhythmia induction during intracardiac electrophysiological study are employed to determine effectiveness of a specific dose of d-sotalol in treating arrhythmias by prolongation of action potential duration. N. Edvardsson, et al., supra.

Pharmaceutically acceptable acid addition salts of d-sotalol are prepared in conventional manner known in the art, for example, by solution of d-sotalol in a suitable solvent and addition of the desired acid, for example, in a stochiometric ratio, and isolation of the salt by standard techniques such as concentration and crystallization. Examples of pharmaceutically acceptable acid addition salts of d-sotalol which may be prepared in this manner include salts of inorganic acids such as sulfuric, nitric, phosphoric, and preferably hydrochloric acid, as well as organic acids such as acetic, propionic, succinic, furmaric, maleic, citric, tartaric, cinnamic, lactic, mandelic, ethanedisulfonic acid and the like.

The pharmaceutical compositions of d-sotalol employed in the process of the instant invention can be prepared in the conventional way using the common carriers, bindary auxiliaries, and solvents. As previously stated, oral administration is preferred and dosage forms compatible therewith are employed. Compositions suitable for oral administration include conventionally prepared solutions, tablets, capsules, drages, etc. prepared from standard pharmaceutical excipients and carriers such as mannitol, milk sugar, organic or inorganic calcium salts, etc., binders such as polyvinylpyrrolidone, gelatin, or cellulose derivatives, as were tablet dissolving agents such as starch or alginic acid, lubricants such as stearic acid, and inorganic flow agents such as talc or colloidal salicylic acid.

As previously stated, d-sotalol is administered at an effective dose that will produce an antiarrhythmic effect by increasing action potential duration without causing any harmful or untoward side effects. An adverse side effect associated with a number of antiarrhythmic agents including quinidine, amiodarone and to some extent dl-sotalol is Torsade de Pointes (also known as polymorphic ventricular tachycardia) which is a clearly defined and easily recognized serious form of unequivocal pro-arrhythmia. By definition, pro-arrhythmia is either the production of a new pattern of ventricular arrhythmia occurring during drug therapy or an existing arrhythmia or aggravation of an existing arrhythmia by drug therapy. When Torsade de Pointes (Torsade) occurs, symptoms such as pre-syncope, syncope (temporary loss of consciousness), palpitations are seen and even death results.

No incidence of Torsade was evident in the clinical evaluation of some 108 patients with serious recurrent supraventricular and ventricular arrhythmias receiving d-sotalol at preferred doses. This constitutes a surprising and unexpected finding since the incidence of Torsade was found to be 4.4% in a similar clinically evaluated group of 298 patients treated with dl-sotalol. Statistical analysis of the two groups by the standard Fisher exact test established that the d-sotalol and dl-sotalol findings were significant (p=0.024) and therefore of substantial clinical importance.

EXAMPLE 1

Resolution of 4-(2-(Isopropylamino-1-hydroxyethyl)methanesulfonanilide d-Sotalol 1-mandelate.—A solution of racemic sotalol (24.5 g., 0.09 mole) (obtained by neutralizing sotalol hydrochloride in ethanol with a mole equivalent of concentrated sodium hydroxide, concentration and extraction of the free base in acetonitrile) in 200 ml. of hot isopropanol was mixed with 13.7 g (0.09 mole) of 1-mandelic acid. On cooling, an optically enriched fraction, 26.0 g., m.p. 125–140°, $[\alpha]_D^{25} -27.2°$, of the d-sotalol·1-mandelate salt was obtained. Crystallization from isopropanol (300 ml.) afforded 18.7 g., m.p. 139–145.5°, $[\alpha]_D^{25} -25.4°$. Further recrystallization of this material from 1:1 isopropanol-absolute ethanol provided d-sotalol·1-mandelate as white fluffy needles, m.p. $154.5 \geq 156°$, $[\alpha]_D^{25} -14.2°$.

Anal Calcd. for $C_{12}H_{20}N_2O_3S \cdot C_8H_8O_3$: C, 56.58; H, 6.65; N, 6.60. Found: C, 56.71; H, 6.82; N, 6.51.

d-Sotalol Hydrochloride.—Acidification of a suspension of d-sotalol·1-mandelate (10.6 g., 0.025 mole $[\alpha]_D^{25} -14.2o$) in 150 ml. of isopropanol with 8 ml. of 3.9N ethanolic hydrogen chloride afforded complete solution at reflux temperature. On cooling 7 0 g (90%) of a white crystalline solid deposited which after crystallization from 20 ml. of methanol and 150 ml. of isopropanol provided 6.0 g (78%) of analytical product, m.p. 204–205.5° (dec ), $[\alpha]_D^{25} +36.0°$.

Anal. Calcd. for $C_{12}N_{20}N_2O_3S \cdot HCl$: C, 46.67; H, 6.85; Cl, 11.48. Found, C, 46.81; H, 6.98; Cl, 11.44.

EXAMPLE 2

Determination of the Purity (Optical Isomer Ratio of d-Sotalol Hydrochloride

A weighed quantity of sample is made basic with 3.6% ammonium hydroxide. The mixture is then saturated with sodium chloride and is absorbed onto Celite 545 (acid-washed diatomaceous earth). This mixture is then placed in a glass chromatographic tube and the free base is eluted from the column with ethylene chloride. A portion of the eluate is evaporated to dryness with a gentle air steam and is shaken for two hours with an acetonitrile solution of 2,3,4,6-tetra-0-acetyl-beta-D-glucopyranosyl isothiocyante. This solution is then diluted with an equal volume of water and subjected to liquid chromatography using an Ultrasphere ODS 5 micrometer column and a mobile phase of acetonitrile:0.02M $(NH_4)H_2PO_4$(40:60) at room temperature. Detection is done at 225 nm and peak areas are obtained using a Hewlett-Packard series 3350 Laboratory Automation System (LAS). The optical isomer ratio (d:l) is calculated from the integrated areas of the two peaks of interest.

EXAMPLE 3

Electrophysiological Effects of Sotalol, d-Sotalol and l-Sotalol

Perfused cardiac Perkinge fibers and guinea pig cardiac papillary muscle were stimulated electrically and transmembrane potentials recorded with glass microelectrodes in conventional manner known to the art. L. D. Davis, et al., *Research In Physiology*, Ed. F. F. Kao, et al., page 99, A. Gaggi, Bologna, 1971.

Evaluation of the test agent was carried out by increasing the concentration in successive steps from $3 \times 10^{-7}M$ up to $3 \times 10^3M$ with each concentration applied during a 30 min. period. The preparations were stimulated at 60/min. and transmembrane potentials measured using standard micro-electrode technique.

At concentration between $3 \times 10^{-7}M$ and $10^{-4}M$, sotalol, d-sotalol and l-sotalol significantly prolonged the action potential duration with nearly identical effects.

EXAMPLE 4 d-Sotalol Class III Action in the Dog

The effects of d-sotalol at $10^{-6}$ to $5 \times 10^{-4}M$ on the action potentials of ventricular muscle and Purkinge fibers from infarcted (Inf.) and non-infarcted (Non-Inf.) areas was determined in 10 dogs four days after coronary ligation with the following effects at $5 \times 10^{-4}M$ concentration shown as mean ± standard deviation.

|  | Ventricular | | Purkinge | |
|---|---|---|---|---|
|  | Non-Inf. | Inf. | Non-Inf. | Inf. |
| Action | | | | |
| Potential Duration: | | | | |
| Control | 219 ± 41 | 173 ± 49 | 278 ± 42 | 338 ± 42 |
| d-sotalol | 250 ± 44* | 201 ± 53* | 372 ± 39* | 419 ± 68* |
| Effective Refractory Period: | | | | |
| Control | 215 ± 24 | 230 ± 37 | 220 ± 37 | 248 ± 44 |
| d-Sotalol | 244 ± 53* | 294 ± 36* | 302 ± 44* | 367 ± 52** |

*p below 0.05 d-sotalol vs. control.

The data demonstrates that in both non-infarcted and infarcted areas, d-sotalol significantly prolonged the action potential duration and that the effective refractory period was significantly more prolonged in the infarcted compared to the non-infarcted areas leading to the conclusion that d-sotalol has significant Class III effects.

What is claimed is:

1. An antiarrhythmic process comprising administering an effective dose of d-sotalol essentially free of l-sotalol or a pharmaceutically acceptable acid addition salt thereof to a human having or susceptable to arrhythmia to lengthen the action potential duration of cardiac cell sufficiently to produce an antiarrhythmic effect without blocking beta-adrenergic receptor sites.

2. The process of claim 1 wherein d-sotalol or a pharmaceutically acceptable acid addition salt thereof is orally administered.

3. The process of claim 1 wherein the effective dose of d-sotalol or a pharmaceutically acceptable acid addition salt thereof ranges from 0.3 to 8.6 mg/kg body weight of said human.

4. The process of claim 1 wherein the effective intravenous dose of d-sotalol or a pharmaceutically acceptable acid addition salt thereof ranges from 0.75 to 2.0 mg/kg body weight.

5. The process of claim 1 wherein the effective oral dose of d-sotalol or a pharmaceutically acceptable acid addition salt thereof ranges from 100 to 200 mg.

* * * * *